United States Patent
Bae et al.

(10) Patent No.: US 12,426,790 B2
(45) Date of Patent: Sep. 30, 2025

(54) APPARATUS AND METHOD FOR ESTIMATING BLOOD PRESSURE

(71) Applicants: SAMSUNG ELECTRONICS CO., LTD., Suwon-si (KR); IUCF-HYU (INDUSTRY-UNIVERSITY COOPERATION FOUNDATION HANYANG UNIVERSITY), Seoul (KR)

(72) Inventors: Sang Kon Bae, Seongnam-si (KR); Joon-Hyuk Chang, Seoul (KR); Youn Ho Kim, Hwaseong-si (KR); Jin Woo Choi, Ansan-si (KR); Jehyun Kyung, Seoul (KR); Joon-Young Yang, Seoul (KR); Ye-Rin Jeoung, Seoul (KR); Jeong-Hwan Choi, Seoul (KR)

(73) Assignees: SAMSUNG ELECTRONICS CO., LTD., Suwon-si (KR); IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 435 days.

(21) Appl. No.: 17/968,309

(22) Filed: Oct. 18, 2022

(65) Prior Publication Data
US 2023/0329566 A1    Oct. 19, 2023

(30) Foreign Application Priority Data
Apr. 19, 2022  (KR) .......................... 10-2022-0048388

(51) Int. Cl.
*A61B 5/021*    (2006.01)
*A61B 5/00*     (2006.01)
*A61B 5/024*    (2006.01)

(52) U.S. Cl.
CPC ...... *A61B 5/02108* (2013.01); *A61B 5/02416* (2013.01); *A61B 5/6843* (2013.01); *A61B 5/7267* (2013.01); *A61B 5/7278* (2013.01)

(58) Field of Classification Search
None
See application file for complete search history.

(56) References Cited

U.S. PATENT DOCUMENTS

2017/0311902 A1    11/2017  Ferber et al.
2018/0132731 A1     5/2018  Albadawi et al.
(Continued)

FOREIGN PATENT DOCUMENTS

KR    10-2019-0106004 A      9/2019
KR       10-2042700 B1      11/2019
(Continued)

OTHER PUBLICATIONS

Communication issued Jul. 26, 2024 by the Korean Intellectual Property Office in the Korean Patent Application No. 10-2022-0048388.
(Continued)

*Primary Examiner* — Shahdeep Mohammed
(74) *Attorney, Agent, or Firm* — Sughrue Mion, PLLC

(57) ABSTRACT

An apparatus for estimating blood pressure includes: a photoplethysmogram (PPG) sensor configured to measure a PPG signal from an object; a force sensor configured to measure a force signal acting between the object and the PPG sensor; and a processor configured to (i) divide a predetermined blood pressure range into a plurality of classes, (ii) input the measured PPG signal and the measured force signal into a blood pressure estimation model to obtain the probability values for each of the classes, and (iii) estimate blood pressure based on the obtained probability values for the respective classes.

13 Claims, 10 Drawing Sheets

(56) References Cited

U.S. PATENT DOCUMENTS

| | | | | |
|---|---|---|---|---|
| 2018/0373925 A1* | 12/2018 | Wang | ............... | G06V 40/172 |
| 2019/0069850 A1 | 3/2019 | Datta et al. | | |
| 2020/0375550 A1 | 12/2020 | Shin | | |
| 2021/0335495 A1 | 10/2021 | Hsiung et al. | | |
| 2022/0015651 A1* | 1/2022 | Bae | ............... | A61B 5/7267 |
| 2022/0361823 A1* | 11/2022 | Goldner | ............ | A61B 5/14514 |
| 2023/0223011 A1* | 7/2023 | Golman | ............... | G10L 15/16 |
| | | | | 704/240 |

FOREIGN PATENT DOCUMENTS

| | | |
|---|---|---|
| KR | 10-2020-0004667 A | 1/2020 |
| KR | 10-2020-0071183 A | 6/2020 |
| KR | 10-2020-0123335 A | 10/2020 |
| KR | 10-2020-0137370 A | 12/2020 |
| KR | 10-2022-0009672 A | 1/2022 |

OTHER PUBLICATIONS

Panwar, Madhuri et al., "PP-Net: A Deep Learning Framework for PPG based Blood Pressure and Heart Rate Estimation", IEEE Sensors Journal, vol. 20, Issue. 17, Sep. 2020. (12 pages total).

Shimazaki, Shota et al., "Cuffless Blood Pressure Estimation from only the Waveform of Photoplethysmography using CNN", Annu Int Conf IEEE Eng Med Biol Soc., Jul. 2019, https://pubmed.ncbi.nlm.nih.gov/31946992/. (1 page total—Abstract).

Baek, Sanghyun et al., "End-to-End Blood Pressure Prediction via Fully Convolutional Networks", IEEE Access, 2019, vol. 7, pp. 185458-185468. (11 pages total).

\* cited by examiner

APPARATUS AND METHOD FOR ESTIMATING BLOOD PRESSURE

CROSS-REFERENCE TO RELATED APPLICATION(S)

This application claims priority from Korean Patent Application No. 10-2022-0048388, filed on Apr. 19, 2022, in the Korean Intellectual Property Office, the entire disclosure of which is incorporated herein by reference for all purposes.

BACKGROUND

1. Field

The following description relates to an apparatus and method for non-invasively estimating blood pressure, and more particularly to technology for estimating blood pressure by using a deep learning-based estimation model.

2. Description of the Related Art

Generally, methods of non-invasively measuring blood pressure without damaging a human body include a cuff-based pressure measuring method and a pulse waves measuring method without the use of a cuff.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a pressure signal changes significantly. Cuffless blood pressure measurement methods generally include a method of estimating blood pressure by calculating a Pulse Transit Time (PTT), and a Pulse Wave Analysis (PWA) method of estimating blood pressure by analyzing the shape of a pulse wave.

SUMMARY

In one general aspect, there is provided an apparatus for estimating blood pressure, the apparatus including: a photoplethysmogram (PPG) sensor configured to measure a PPG signal from an object; a force sensor configured to measure a force signal acting between the object and the PPG sensor; and a processor configured to (i) divide a predetermined blood pressure range into a plurality of classes, (ii) input the measured PPG signal and the measured force signal into a blood pressure estimation model to obtain probability values for each of the classes, and (iii) estimate blood pressure based on the obtained probability values for the respective classes.

In this case, the blood pressure estimation model may be based on at least one of Deep Neural Network (DNN), Convolution Neural Network (CNN), and Recurrent Neural Network (RNN).

The processor may be configured to obtain a blood pressure value by calculating an inner product between a vector of the probability values for the respective classes and a vector of representative values for the respective classes.

The processor may be configured to set, as the representative value for the respective classes, at least one of a median value, a mean value, a maximum value, and a minimum value in a blood pressure range of the respective classes.

The blood pressure estimation model may include a first convolution layer to which the PPG signal is input, a second convolution layer to which the force signal is input, a first pooling layer connected to the first convolution layer, a second pooling layer connected to the second convolution layer, a connected layer connecting an output of the first pooling layer and an output of the second pooling layer to output a feature, and a dense layer outputting probability values for the respective classes by using the feature as an input.

The processor may be configured to collect a plurality of training data including training signals, including a training PPG signal and a training force signal, and a target blood pressure, may construct a training dataset for the respective classes by labeling the target blood pressure of the collected training data according to the respective classes, and may be configured to train the blood pressure estimation model based on deep learning by using the constructed training dataset.

The processor may be configured to perform one-hot encoding on classes of the labeled target blood pressure, and may construct the training dataset including a result of the one-hot encoding and the training signals.

By using a cross-entropy loss function, the processor may be configured to train the blood pressure estimation model so that a loss between a probability value of a ground truth class and a probability value of a predicted class, which is output by the blood pressure estimation model, may be minimized.

By using an additive margin softmax loss function, the processor may be configured to train the blood pressure estimation model so that a loss between a probability value of a ground truth class and a probability value of a predicted class, which is output by the blood pressure estimation model, may be minimized.

In addition, the apparatus for estimating blood pressure may further include an output interface configured to provide a user with information on the estimated blood pressure through at least one of a display, an audio output device, and a haptic device.

In another general aspect, there is provided a method of estimating blood pressure, the method including: measuring a photoplethysmogram (PPG) signal for estimating blood pressure from an object; measuring a force signal acting between the object and a PPG sensor during measurement of the PPG signal for estimating blood pressure; dividing a predetermined blood pressure range into a plurality of classes, inputting the measured PPG signal and the measured force signal into a blood pressure estimation model to obtain probability values for each of the respective classes; and estimating blood pressure based on the obtained probability values for the respective classes.

The blood pressure estimation model may be based on at least one of Deep Neural Network (DNN), Convolution Neural Network (CNN), and Recurrent Neural Network (RNN).

The estimating of the blood pressure may include obtaining a blood pressure value by calculating an inner product between a vector of the probability values for the respective classes and a vector of representative values for the respective classes.

The representative value for the respective classes may be set as at least one of a median value, a mean value, a maximum value, and a minimum value in a blood pressure range of the respective classes.

In this case, the blood pressure estimation model may include a first convolution layer to which the PPG signal is input, a second convolution layer to which the force signal is input, a first pooling layer connected to the first convolution layer, a second pooling layer connected to the second convolution layer, a connected layer connecting an output of the first pooling layer and an output of the second pooling layer to output a feature, and a dense layer outputting probability values for the respective classes by using the feature as an input.

In addition, the method of estimating blood pressure may further include: collecting a plurality of training data including training signals, including a training PPG signal and a training force signal, and a target blood pressure; constructing a training dataset for the respective classes by labeling the target blood pressure of the collected training data according to the respective classes; and training the blood pressure estimation model based on deep learning by using the constructed training dataset.

The constructing of the training dataset may include performing one-hot encoding on classes of the labeled target blood pressure, and constructing a training dataset including a result of the one-hot encoding and the training signals.

The training of the blood pressure estimation model may include, by using a cross-entropy loss function, training the blood pressure estimation model so that a loss between a probability value of a ground truth class and a probability value of a predicted class, which is output by the blood pressure estimation model, may be minimized.

The training of the blood pressure estimation model may include, by using an additive margin softmax loss function, training the blood pressure estimation model so that a loss between a probability value of a ground truth class and a probability value of a predicted class, which is output by the blood pressure estimation model, may be minimized.

In yet another general aspect, there is provided an electronic device including: a memory for storing computer-readable instructions; and a processor configured to estimate blood pressure by executing the instructions, wherein the processor may be configured to divide a predetermined blood pressure range into a plurality of classes, to obtain probability values for each of the classes by inputting a PPG signal, measured from a user, and a force signal, representing an external force acting on the electronic device during measurement of the PPG signal, to a blood pressure estimation model which is trained to output the probability values for the respective classes, and to estimate blood pressure based on the obtained probability values for the respective classes.

Figure 1:
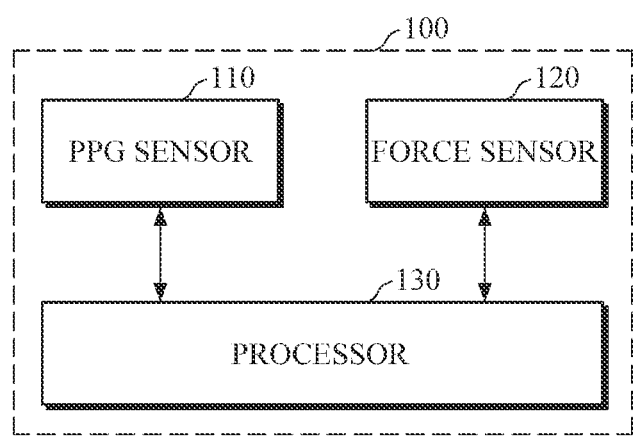
FIG. 1 is a block diagram illustrating an apparatus for estimating blood pressure according to an embodiment of the present disclosure.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Details of other embodiments are included in the following detailed description and drawings. Advantages and features of the present invention, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as "unit" or "module", etc., should be understood as a unit for performing at least one function or operation and that may be embodied as hardware, software, or a combination thereof.

Hereinafter, various embodiments of an apparatus and method for estimating blood pressure will be described in detail with reference to the accompanying drawings. Various embodiments of the apparatus for estimating blood pressure may be included in electronic devices, such as a smartphone, tablet PC, a desktop computer, a laptop computer, or wearable devices such as wristwatch-type wearable device, a bracelet-type wearable device, a wristband-type wearable device, a ring-type wearable device, a glasses-type wearable device, an earphone-type wearable device, a necklace-type wearable device, an anklet-type wearable device, a headband-type wearable device, and the like. The embodiments which will be described below may be modified to estimate a variety of bio-information including not only blood pressure, but also vascular age, arterial stiffness, aortic pressure waveform, vascular compliance, stress index, fatigue level, skin age, skin elasticity, and other physiological indicators.

FIG. 1 is a block diagram illustrating an apparatus for estimating blood pressure according to an embodiment of the present disclosure.

Referring to FIG. 1, an apparatus 100 for estimating blood pressure includes a photoplethysmography (PPG) sensor 110, a force sensor 120, and a processor 120.

The PPG sensor 110 may measure a PPG signal upon contact with an object. In this case, the object may be a body part where pulse waves may be easily measured by the PPG sensor 110 upon contact with the body part. For example, the object may be a finger (an example area where blood vessels are densely innervated in the body), but is not limited thereto, and may be a surface of the wrist that is adjacent to the radial artery, an upper part of the wrist where venous blood or capillary blood passes, carotid region of the neck, or another part of the body, such as toes and dorsum of the foot.

The PPG sensor 110 may include one or more light sources for emitting light toward the object and one or more detectors for detecting light scattered or reflected from or transmitted through the object after light is emitted by the light sources. In this case, the light source may include a light emitting diode (LED), a laser diode (LD), a phosphor, and the like. The light sources may emit light of one or more wavelengths (e.g., green, red, blue, and infrared wavelengths). In addition, the detectors may include one or more photodiodes, photo transistors (PTr), image sensors (e.g., complementary metal-oxide semiconductor (CMOS) image sensor), etc., but is not limited thereto.

The force sensor 120 may measure a force signal acting between the object and the PPG sensor 110 while the PPG sensor 110 measures the PPG signal from the object. For example, when a user places the object on the PPG sensor 110 and gradually increases/decreases a pressing force for inducing a change in pulse wave amplitude, the force sensor 120 may detect a change in contact force. The force sensor 120 may be disposed over or under the PPG sensor 110. The force sensor 120 may be formed as a single force sensor such as a strain gauge or a piezoelectric sensor, or may be formed as a force sensor array. However, the force sensor 120 is not limited thereto, and instead of the force sensor 120, an air bladder type pressure sensor, a pressure sensor in combination with a force sensor and an area sensor, and the like may be provided. Accordingly, the term "force" used herein may refer to "force" or "pressure."

The processor 130 may be electrically connected to the PPG sensor 110 and/or the force sensor 120, and may control the PPG sensor 110 and/or the force sensor 120. Upon receiving the PPG signal from the PPG sensor 110, the processor 130 may perform preprocessing, such as removing noise from the received PPG signal. For example, the processor 130 may perform signal correction, such as low-pass filtering, band-pass filtering (e.g., filtering between 0.4 Hz and 10 Hz), amplification of the bio-signal, converting the signal into a digital signal, smoothing, ensemble averaging of a continuously measured PPG signal, and other forms of signal processing. In addition, the processor 130 may obtain a plurality of unit waveforms by segmenting a waveform of a PPG signal, measured continuously during a predetermined period of time, into cycles, and may determine a representative waveform for use in estimating blood pressure by using any one or a combination of two or more of the plurality of unit waveforms.

Upon receiving the PPG signal and the force signal for estimating blood pressure from the PPG sensor 110 and the force sensor 120, the processor 130 may estimate blood pressure by using a blood pressure estimation model. In this case, the blood pressure estimation model may be a neural network model based on Deep Neural Network (DNN), Convolution Neural Network (CNN), Recurrent Neural Network (RNN), and other artificial neural networks (ANN). As will be described in detail below, a blood pressure estimation model 200 may be trained based on deep learning to divide a blood pressure range into a plurality of classes and to output a probability value vector representing a corresponding probability for each of the classes.

As used in this disclosure, A DNN may be an ANN with multiple layers between the input and output layers. A DNN includes components such as neurons, synapses, weights, biases, and functions. These components as a whole function similarly to a human brain, and can be trained like other ML algorithms.

For example, a DNN that is trained to recognize dog breeds will go over the given image and calculate the probability that the dog in the image is a certain breed. The user can review the results and select which probabilities the network should display (above a certain threshold, etc.) and return the proposed label. Each mathematical manipulation as such is considered a layer, and complex DNN have many layers.

DNNs can be used to model complex non-linear relationships. DNN architectures generate compositional models where the object is expressed as a layered composition of primitives. The extra layers enable composition of features from lower layers, potentially modeling complex data with fewer units than a similarly performing shallow network. For instance, it was proved that sparse multivariate polynomials are exponentially easier to approximate with DNNs than with shallow networks.

Deep architectures include many variants of a few basic approaches. Each architecture has found success in specific domains. It is not always possible to compare the performance of multiple architectures, unless they have been evaluated on the same data sets.

DNNs are typically feedforward networks in which data flows from the input layer to the output layer without looping back. At first, the DNN creates a map of virtual neurons and assigns random numerical values, or "weights", to connections between them. The weights and inputs are multiplied and return an output between 0 and 1. If the network did not accurately recognize a particular pattern, an algorithm would adjust the weights. That way the algorithm can make certain parameters more influential, until it determines the correct mathematical manipulation to fully process the data.

As used in this disclosure, a RNN may be a class of ANN where connections between nodes can create a cycle, allowing output from some nodes to affect subsequent input to the same nodes. This allows it to exhibit temporal dynamic behavior. Derived from feedforward neural networks, RNNs can use their internal state (memory) to process variable length sequences of inputs. This makes them applicable to tasks such as pattern recognition. RNNs are theoretically Turing complete and can run arbitrary programs to process arbitrary sequences of inputs.

The term "recurrent neural network" is used to refer to the class of networks with an infinite impulse response, whereas "convolutional neural network" refers to the class of finite impulse response. Both classes of networks exhibit temporal dynamic behavior. A finite impulse recurrent network is a directed acyclic graph that can be unrolled and replaced with a strictly feedforward neural network, while an infinite impulse recurrent network is a directed cyclic graph that cannot be unrolled.

Both finite impulse and infinite impulse recurrent networks can have additional stored states, and the storage can be under direct control by the neural network. The storage can also be replaced by another network or graph if that incorporates time delays or has feedback loops. Such controlled states are referred to as gated state or gated memory, and are part of long short-term memory networks (LSTMs) and gated recurrent units. This is also called Feedback Neural Network (FNN).

As used in this disclosure, CNN may be a class of ANN, that while commonly applied to analyze visual imagery, may also be used in a variety of other applications. CNNs are also known as Shift Invariant or Space Invariant Artificial Neural Networks (SIANN), based on the shared-weight architecture of the convolution kernels or filters that slide along input features and provide translation-equivariant responses known as feature maps. Counter-intuitively, most convolutional neural networks are not invariant to translation, due to the downsampling operation they apply to the input.

CNNs are regularized versions of multilayer perceptrons. Multilayer perceptrons usually mean fully connected networks, that is, each neuron in one layer is connected to all neurons in the next layer. The "full connectivity" of these networks make them prone to overfitting data. Typical ways of regularization, or preventing overfitting, include: penalizing parameters during training (such as weight decay) or trimming connectivity (skipped connections, dropout, etc.) CNNs take a different approach towards regularization: they take advantage of the hierarchical pattern in data and assemble patterns of increasing complexity using smaller and simpler patterns embossed in their filters. Therefore, on a scale of connectivity and complexity, CNNs are on the lower extreme.

Convolutional networks were inspired by biological processes in that the connectivity pattern between neurons resembles the organization of the animal visual cortex. Individual cortical neurons respond to stimuli only in a restricted region of the visual field known as the receptive field. The receptive fields of different neurons partially overlap such that they cover the entire visual field.

CNNs use relatively little pre-processing compared to other image classification algorithms. This means that the network learns to optimize the filters (or kernels) through automated learning, whereas in traditional algorithms these filters are hand-engineered. This independence from prior knowledge and human intervention in feature extraction is a major advantage.

Figure 2:
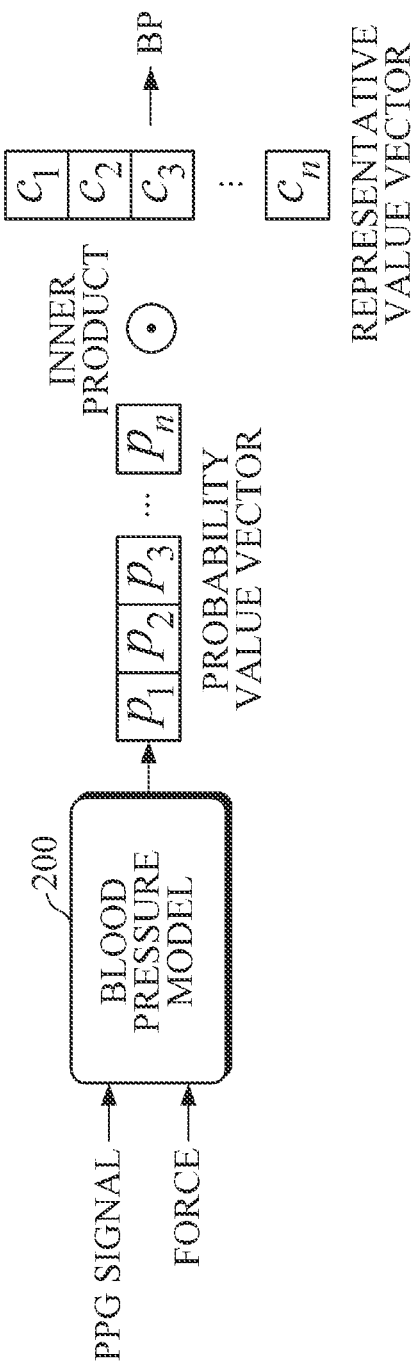
FIG. 2 is a diagram explaining an example of estimating blood pressure.
Figure 3:
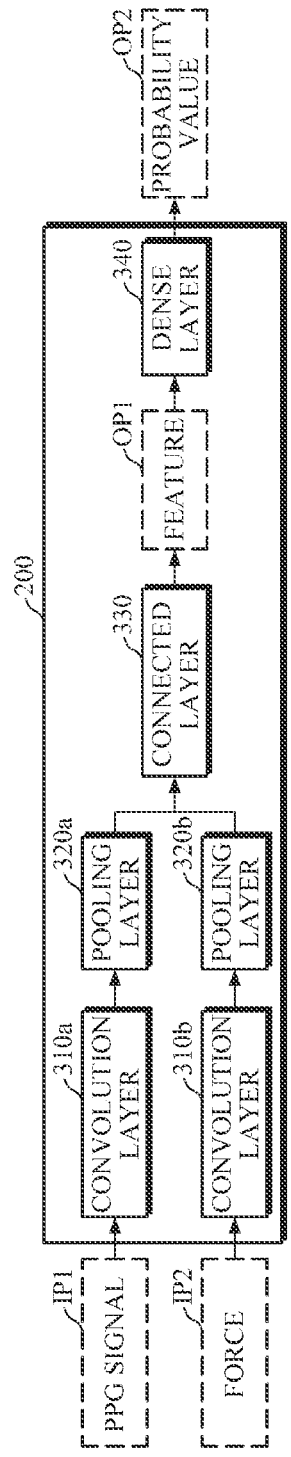
FIG. 3 is a block diagram illustrating an example of a blood pressure estimation model.

FIG. 2 is a diagram explaining an example of estimating blood pressure. FIG. 3 is a block diagram illustrating an example of a blood pressure estimation model.

Referring to FIGS. 1 and 2, the processor 130 may input the PPG signal and the force signal to the blood pressure estimation model 200, and once the blood pressure estimation model 200 processes the PPG signal and the force signal and outputs probability values $p_1, p_2, p_3, \ldots,$ and $p_n$ for each class, the processor 130 may obtain a final blood pressure value by using a vector of the output probability values $p_1, p_2, p_3, \ldots,$ and $p_n$. For example, by calculating an inner product between the vector of the probability values $p_1, p_2, p_3, \ldots,$ and $p_n$ for each class and a vector of predefined representative values $c_1, c_2, c_3, \ldots,$ and $c_n$ for each class, the processor 130 may determine a resultant value as a final blood pressure value. In this case, the representative values $c_1, c_2, c_3, \ldots,$ and $c_n$ for each class may be defined as values obtained by internally dividing in a specific ratio a median value, a mean value, a maximum value, and a minimum value, or a minimum value and a maximum value, in a blood pressure range of each class.

Referring to FIG. 3, in the blood pressure estimation model 200, in some embodiments, may include convolution layers 310a and 310b, pooling layers 320a and 320b, a connected layer 330, a dense layer 340 in a sequentially disposed manner.

As used in this disclosure, a convolutional layer (such as convolution layers 310a and 310b) may be the core building block of a CNN. The layer's parameters include a set of learnable filters (or kernels), which have a small receptive field, but extend through the full depth of the input volume. During the forward pass, each filter is convolved across the width and height of the input volume, computing the dot product between the filter entries and the input, producing a 2-dimensional activation map of that filter. As a result, the network learns filters that activate when it detects some specific type of feature at some spatial position in the input.

Stacking the activation maps for all filters along the depth dimension forms the full output volume of the convolution layer. Every entry in the output volume can thus also be interpreted as an output of a neuron that looks at a small region in the input and shares parameters with neurons in the same activation map.

As seen in FIG. 3, A PPG signal IP1 and a force signal IP2 may be input to a first convolution layer 310a and a second convolution layer 320a, respectively, and the respective convolution layers 310a and 310b may perform convolution operation for dimensional reduction of the PPG signal and the force signal.

As used in this disclosure, a pooling layer (such as first pooling layer 320a and second pooling layer 320b) may be a form of non-linear down-sampling. There are several non-linear functions to implement pooling, where max pooling is the most common. It partitions the input image into a set of rectangles and, for each such sub-region, outputs the maximum.

Intuitively, the exact location of a feature is less important than its rough location relative to other features. This is the idea behind the use of pooling in convolutional neural networks. The pooling layer serves to progressively reduce the spatial size of the representation, to reduce the number of parameters, memory footprint and amount of computation in the network, and hence to also control overfitting. This is known as down-sampling. It is common to periodically insert a pooling layer between successive convolutional layers (each one typically followed by an activation function, such as a ReLU layer) in a CNN architecture. While pooling layers contribute to local translation invariance, they do not provide global translation invariance in a CNN, unless a form of global pooling is used. The pooling layer commonly operates independently on every depth, or slice, of the input and resizes it spatially.

As seen in FIG. 3, A first pooling layer 320a and a second pooling layer 320b may perform pooling operation by using outputs of the first convolution layer 310a and the second convolution layer 310b, respectively, as inputs. In this case, the pooling layers 320a and 320b may perform statistics pooling (e.g., max pooling or average pooling). The connected layer 330 may connect outputs of the respective pooling layers 320a and 320b to output a feature OP1. In this case, the feature OP1 may be a feature vector including one or more features. The dense layer 340 outputs probability values OP2 for each of n number of classes by receiving the feature OP1 output from the connected layer 330.

Additionally, the processor 120 may collect user characteristic information (e.g., a user's age, gender, stature, weight, and other health related information). For example, the processor 120 may provide a user with an interface to receive input of user characteristic information from the user through the interface. Alternatively, the processor 120 may be connected to other applications, managing the user characteristic information, to collect necessary information.

By further considering the collected user characteristic information, the processor 120 may obtain a final blood pressure. For example, the blood pressure estimation model may be trained to output probability values for each class by using the user characteristic information as an input, in addition to the PPG signal and the force signal. In this case, the processor 120 may obtain a blood pressure value by inputting the collected user characteristic information along with the PPG signal and the force signal to the blood pressure estimation model, and by calculating an inner product between the probability values for each class, which are outputs of the blood pressure estimation models, and the representative values for each class.

Figure 4:
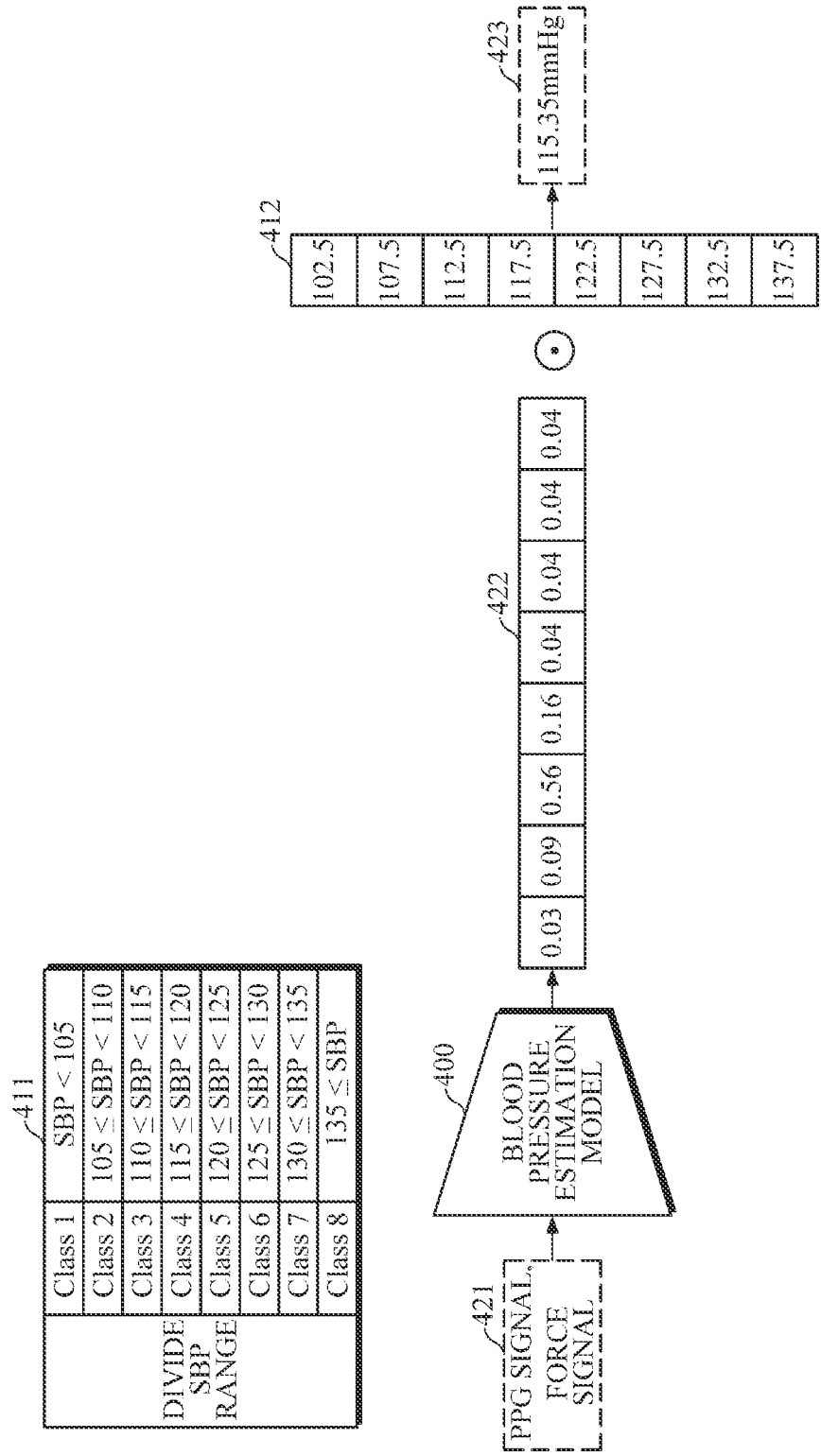
FIG. 4 is a diagram explaining an example of generating a blood pressure estimation model.

FIG. 4 is a diagram explaining an example of generating a blood pressure estimation model.

Referring to FIGS. 1 and 4, the processor 130 may collect a plurality of training data for a predetermined period of time from a plurality of users or a specific user. The training data may include training signals, including a training PPG signal and a training force signal, and a target blood pressure corresponding to the training signals. By controlling the PPG sensor 110 and the force sensor 120, the processor 130 may obtain the training PPG signal and force signal from the plurality of users or the specific user. Alternatively, through a communication module, the processor 130 may receive the training PPG signal and force signal from other apparatuses for estimating blood pressure, which are used by the respective users.

The processor 130 may limit a range of blood pressure values to be predicted to a specific range, and may divide the limited specific range in predetermined units so that the range may be divided into a plurality of classes. For example, assuming that a normal blood pressure group is collected, the processor 130 may limit a systolic blood pressure range to a range of 100 mmHg to 140 mmHg, and may divide the systolic blood pressure range in units of 5 mmHg into eight classes 411. In this case, the limited range of blood pressure values may be set to various ranges by considering blood pressure groups of the collected training data and/or a health condition (e.g. whether a user has low blood pressure, normal blood pressure, or high blood pressure) of a user using the apparatus 100 for estimating blood pressure, and the like.

In addition, the processor 130 may set representative values 412 for each of the divided classes 411. In this case, the representative value of each class may be a median value in the blood pressure range of each class 411, as illustrated in FIG. 4. However, the representative value is not limited thereto, and the processor 130 may set, as the representative value, a value obtained by internally dividing a mean value, a maximum value, and a minimum value, or a minimum value and a maximum value, in a specific ratio.

Then, the processor 130 may label a target blood pressure of the training data according to the range of each class. In addition, upon performing one-hot encoding on classes of the labeled target blood pressure, the processor 130 may construct a training dataset including a result of the one-hot encoding and the training signals. Subsequently, by using the training dataset, the processor 130 may train a blood pressure estimation model 400 based on deep learning.

For example, the processor 130 may input a training signal 421 of the entire training dataset to the blood pressure estimation model 400, and may train the blood pressure estimation model 400 to output probability values 422 for each class. That is, the processor 130 may train the blood pressure estimation model 400, so that a weighted sum of the representative values of the classes may be predicted as a correct blood pressure value 423, by using the probability value 422 of each class as a weight for the representative value 412 of each corresponding class.

In this case, by using, for example, a cross-entropy loss function, the processor 130 may train the blood pressure estimation model 400 so that a loss between a probability value of a ground truth class and a probability value of a predicted class may be minimized. In another example, by using an additive margin (AM) softmax loss function, the processor 130 may train the blood pressure estimation model 400 so that a loss between a probability value of a ground truth class and a probability value of a predicted class may be minimized.

Additionally, the processor 130 may further collect user characteristic information of the plurality of users or the specific user as training data. In this manner, the processor 130 may build a blood pressure estimation model using the user characteristic information as an input along with the training signal, and may train the blood pressure estimation model to output probability values for each class, for example, as described above.

In this embodiment, by building a blood pressure estimation model based on a classification task instead of a general regression task, and by using the cross-entropy loss function or the additive margin softmax loss function instead of a general mean squared error loss function, it is possible to reduce significant errors in predicting blood pressure, such as in the case where a high blood pressure sample is predicted as low blood pressure, or vice versa. Particularly, the additive margin softmax loss function may improve the separability of the classes and may make the distance between the same classes more compact, thereby obtaining a more accurate classification effect.

Figure 5:
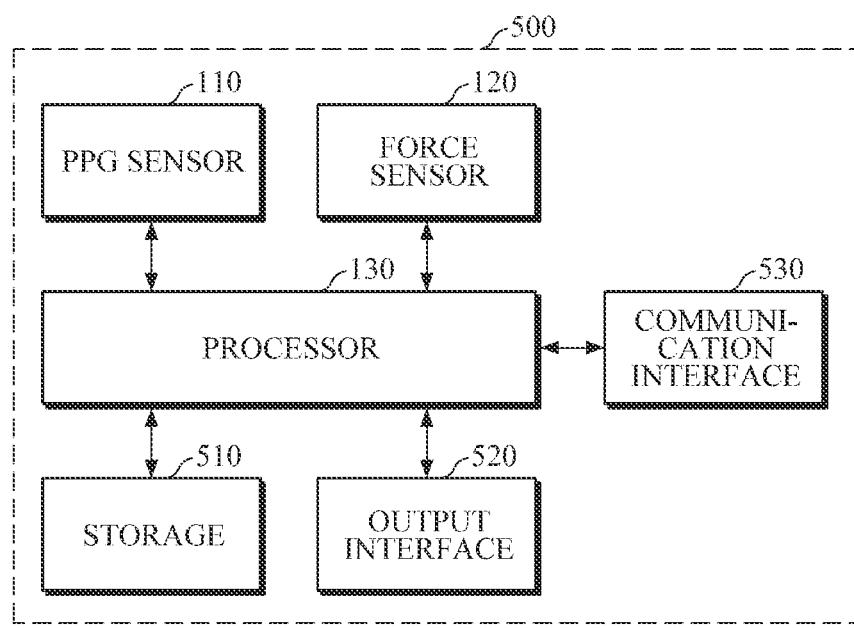
FIG. 5 is a block diagram illustrating an apparatus for estimating blood pressure according to another embodiment of the present disclosure.

FIG. 5 is a block diagram illustrating an apparatus for estimating blood pressure according to another embodiment of the present disclosure.

Referring to FIG. 5, an apparatus 500 for estimating blood pressure may include the PPG sensor 110, the force sensor 120, the processor 130, a storage 510, an output interface 520, and a communication interface 530. The PPG sensor 110, the force sensor 120, and the processor 130 are described in detail above, and thus the following description will be focused on non-redundant features.

The storage 510 is configured to store a variety of information related to estimating blood pressure. For example, the storage 510 may store data processed by the PPG sensor 110, the force sensor 120, and the processor 130. For example, the storage 510 may store a user's PPG signal, force signal, and/or estimated blood pressure value, as well as a blood pressure estimation model or user characteristic information. The storage 510 may include at least one type storage medium such as a flash memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and other non-transitory mediums for storing electronic data, but is not limited thereto.

The output interface 520 may output processing results of the PPG sensor 110, the force sensor 120, and/or the processor 130 and may provide the results to a user. The output interface 520 may provide the user with information by various visual/non-visual methods using a visual output module such as a display, an audio output module such as a speaker, or a haptic module outputting signals such as vibrations and tactile sensation. For example, the output interface 520 may display an estimated blood pressure value on a display. In this case, if the estimated blood pressure value falls outside a normal range, the output interface 520 may provide the user with warning information by changing color, line thickness, etc., or displaying an abnormal value along with the normal range, so that the user may easily recognize the abnormal value.

The communication interface 530 may transmit and receive necessary information with another electronic device by using communication techniques under the control of the processor 130, and the received data may be stored in the storage 510. For example, the communication interface 530 may receive, as a training signal, the PPG signal and the force signal, which are measured by an apparatus for estimating blood pressure included in another electronic device, and may receive cuff blood pressure, measured by an apparatus for measuring blood pressure such as a cuff sphygmomanometer, as the target blood pressure. In addition, the communication interface 530 may receive user characteristic information, such as user health information, from a cloud device managing a user's health condition. Further, the communication interface 530 may transmit an estimated blood pressure value to another electronic device, so that the blood pressure value may be provided to a user through the electronic device. Here, examples of the electronic device may include a smartphone, a tablet PC, a desktop computer, a laptop computer, a wearable device, an apparatus for estimating blood pressure such as a cuff sphygmomanometer, etc., but is not limited thereto.

The communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G, 4G, and 5G communications, and other forms of electronic communication.

Figure 6:
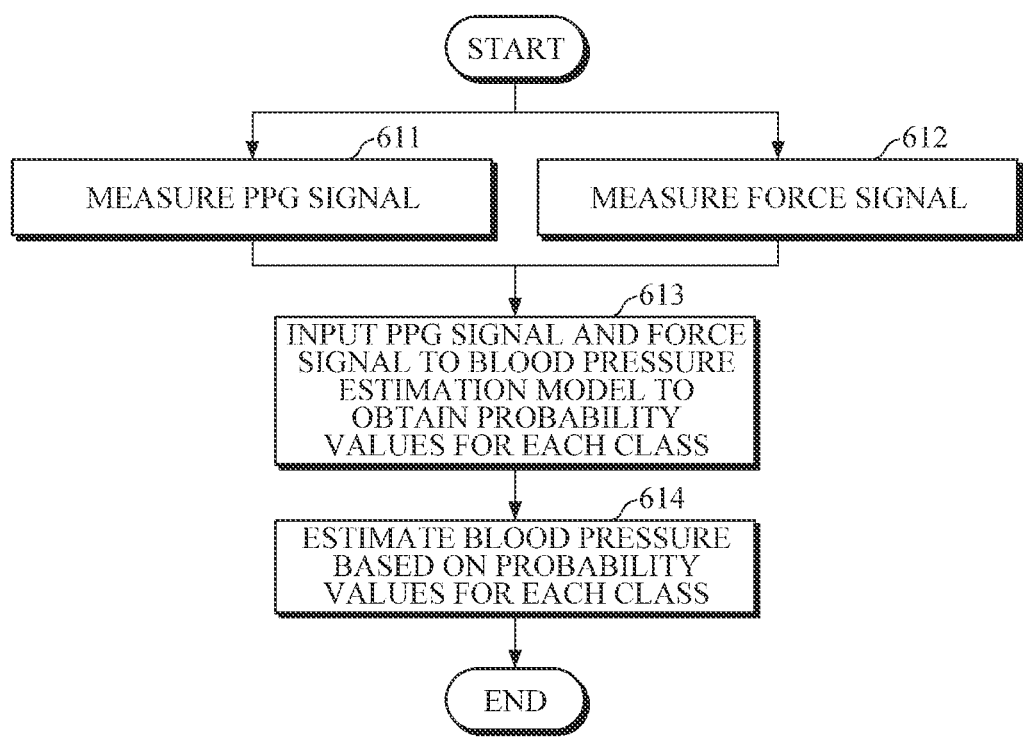
FIG. 6 is a flowchart illustrating a method of estimating blood pressure according to an embodiment of the present disclosure.

FIG. 6 is a flowchart illustrating a method of estimating blood pressure according to an embodiment of the present disclosure.

The method of FIG. 6 is an example of a method of estimating blood pressure performed by the apparatuses 100 and 500 for estimating blood pressure, which are described in detail above, and thus will be briefly described below.

First, the apparatus for estimating blood pressure may measure a PPG signal in step 611 by using the PPG sensor when an object is placed on the PPG sensor, and may measure a force signal, indicative of a change in force applied by the object to the PPG sensor, in step 612 by using the force sensor during measurement of the PPG signal.

Then, the apparatus for estimating blood pressure may input the PPG signal and the force signal to a blood pressure estimation model to obtain probability values for each class in step 613. In this case, the blood pressure estimation model may be a neural network model based on classification task, and may be a model trained based on deep learning to divide a blood pressure range into a plurality of classes and to output probability values for each of the classes by using the PPG signal and the force signal as inputs. In this case, by using a cross-entropy loss function or an additive margin softmax loss function, the blood pressure estimation model may be trained so that a loss between the probability values may be minimized.

Subsequently, the apparatus for estimating blood pressure may estimate blood pressure in 614 based on the probability values output in 613 for each of the classes. For example, the apparatus for estimating blood pressure may determine, as a final blood pressure value, a scalar value obtained by calculating an internal product between a vector of the probability values of each class and a vector of the predefined representative values of each class. In this case, the representative value of each class may be a value obtained by internally dividing in a specific ratio a median value, a mean value, a maximum value, and a minimum value, or a minimum value and a maximum value, in the blood pressure range of each class.

Figure 7:
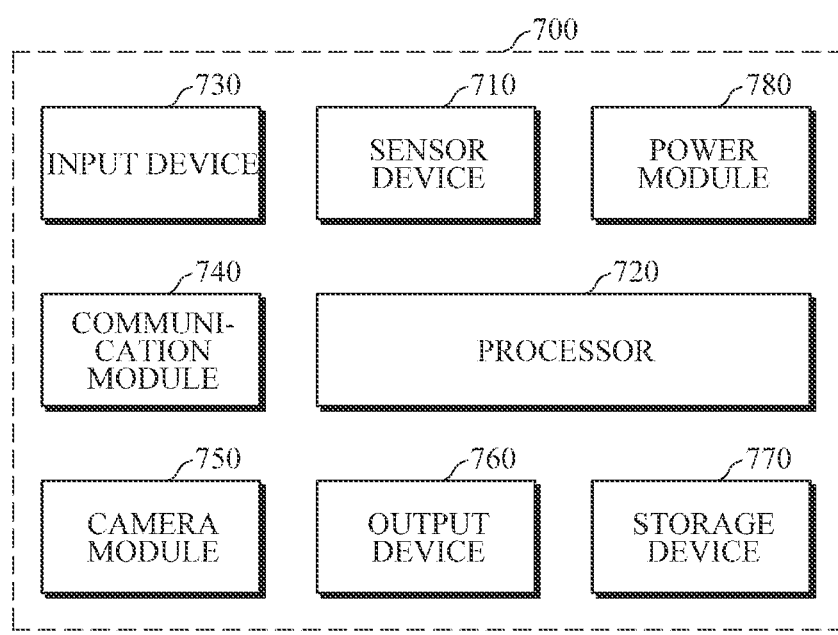
FIG. 7 is a block diagram illustrating an electronic device according to an embodiment of the present disclosure.

FIG. 7 is a block diagram illustrating an electronic device according to an embodiment of the present disclosure.

The electronic device according to an embodiment includes the aforementioned apparatuses 100 and 500 for estimating blood pressure may be implemented as (i) wearable devices such as a smart watch, a smart band, smart glasses, smart earphones, a smart ring, a smart patch, a smart necklace, a smart bracelet, and a smart anklet, or (ii) mobile devices such as a smartphone or a tablet PC, or (iii) home appliances such as a refrigerator or a microwave oven, or (iv) various Internet of Things (IoT) devices (e.g., home IoT device) based on Internet of Things (IoT) technology.

Referring to FIG. 7, an electronic device 700 may include a sensor device 710, a processor 720, an input device 730, a communication module 740, a camera module 750, an output device 760, a storage device 770, and a power module 780. All the components of the electronic device may be integrally mounted in a specific device or may be distributed in two or more devices.

The sensor device 710 may include the PPG sensor and the force sensor of the aforementioned apparatuses 100 and 500 for estimating blood pressure, and may further include sensors for various functions provided by the electronic device 700, e.g., a gyro sensor, a Global Positioning System (GPS), a gas sensor, a temperature/humidity sensor, a proximity sensor, an illumination sensor, a gravity sensor, an acceleration sensor, a geomagnetic sensor, an ultrasonic sensor, and other sensors configured to detect physiologically related information.

The processor 720 may be configured to execute programs, computer-readable instructions, and the like stored in the storage device 770, to control components connected to the processor 720, and may perform various data processing or computation, including the aforementioned operations related to estimating blood pressure. The processor 720 may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), which is operable independently from, or in conjunction with, the main processor.

The input device 730 may be configured to receive a command and/or data to be used by each component of the electronic device, from, for example, a user. The input device 730 may include, for example, a microphone, a mouse, a keyboard, or a digital pen (e.g., a stylus pen). For example, the input device 730 may receive commands related to blood pressure estimation and/or user characteristic information from a user, and may transmit the information to the processor 720 or may store the information in the storage device 770.

The communication module 740 may be configured to support establishment of a direct (e.g., wired) communication channel and/or a wireless communication channel between the electronic device 700 and other electronic device, a server, or the sensor device within a network environment, and performing of communication via the established communication channel. The communication module 740 may include one or more communication processors that are operable independently from the processor and supports a direct communication and/or a wireless communication. The communication device 720 may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 700 in a communication network by using subscriber information (e.g., international mobile subscriber identity (IMSI)) stored in a subscriber identification module.

The camera module 750 may be configured to capture still images or moving images. The camera module 750 may include a lens assembly having one or more lenses, image sensors, image signal processors, and/or flashes. The lens assembly included in the camera module 750 may collect light emanating from a subject to be imaged.

The output device 760 may be configured to visually/non-visually output data generated or processed by the electronic device 700. The output device 760 may include a sound output device, a display device, an audio module, and/or a haptic module.

The sound output device may be configured to output sound signals to the outside of the electronic device 700. The sound output device may include a speaker and/or a receiver. The speaker may be used for general purposes, such as playing multimedia or playing record, and the receiver may be used for incoming calls. The receiver may be implemented separately from, or as part of, the speaker.

The display device may be configured to visually provide information to the outside of the electronic device 700. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may be configured to convert a sound into an electrical signal or vice versa. The audio module may obtain the sound via the input device, or may output the sound via the sound output device, and/or a speaker and/or a headphone of another electronic device directly or wirelessly connected to the electronic device 700.

The haptic module may be configured to convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage device 770 may be configured to store driving conditions required for driving the sensor device 710, and various data required for other components of the electronic device 700. The various data may include, for example, software and input data and/or output data for a command related thereto. The storage device 770 may include a volatile memory and/or a non-volatile memory.

The power module 780 may manage power supplied to the electronic device. The power module may be implemented as part of, for example, a power management integrated circuit (PMIC). The power module 780 may include a battery, which may include a primary cell which is not rechargeable, a secondary cell which is rechargeable, and/or a fuel cell.

Figure 8:
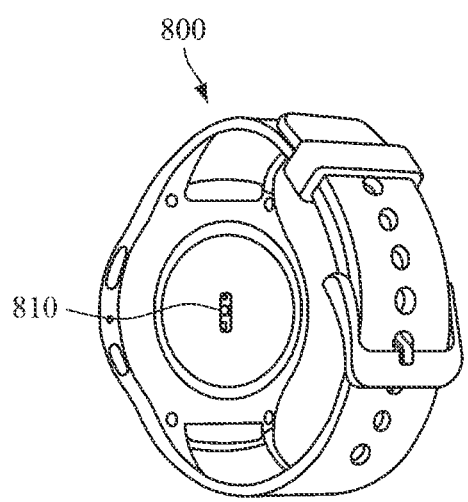
FIGS. 8 to 10 are block diagrams illustrating examples of structures of an electronic device.
Figure 9:
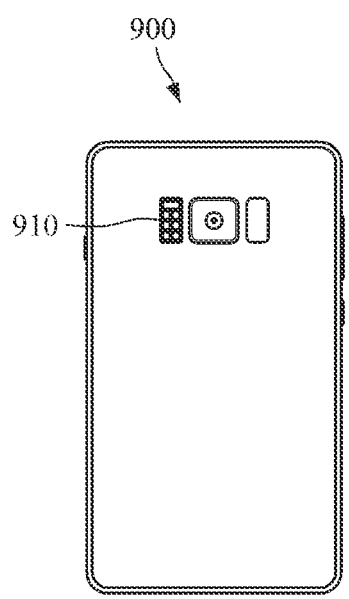
Figure 10:
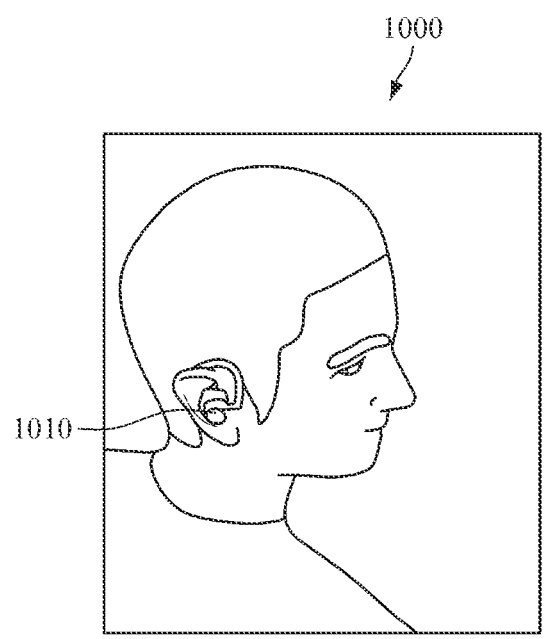

FIGS. 8 to 10 are block diagrams illustrating examples of structures of the electronic device of FIG. 7.

Referring to FIG. 8, the electronic device 700 may be implemented as a wristwatch wearable device 800, and may include a main body and a wrist strap. A display is provided on a front surface of the main body, and may display various application screens, including time information, received message information, and the like. A sensor device 810 may be disposed on a rear surface of the main body, and may measure a PPG signal and a force signal for estimating blood pressure.

Referring to FIG. 9, the electronic device 700 may be implemented as a mobile device 900 such as a smartphone. The mobile device 900 may include a housing and a display panel. The housing may form an outer appearance of the mobile device 900. The housing has a first surface, on which a display panel and a cover glass may be disposed sequentially, and the display panel may be exposed to the outside through the cover glass. A sensor device 910, a camera module and/or an infrared sensor, and the like may be disposed on a second surface of the housing. The processor and various other components may be disposed in the housing.

Referring to FIG. 10, the electronic device 700 may be implemented as an ear-wearable device 1000.

The ear-wearable device 1000 may include a main body and an ear strap. A user may wear the ear-wearable device 1000 by hanging the ear strap on the auricle. The ear strap may be omitted depending on a shape of the ear-wearable device 1000. The main body may be inserted into the external auditory meatus. A sensor device 1010 may be mounted in the main body. Further, the processor may be disposed in the main body, and may estimate blood pressure by using a PPG signal and a force signal which are measured by the sensor device 1010. Alternatively, the ear-wearable device 1000 may estimate blood pressure by interworking with an external device. For example, the ear-wearable device 1000 may transmit the PPG signal, measured by the sensor device 1010 of the ear-wearable device 1000, to an external device, e.g., a smartphone, a tablet PC, etc., through a communication module provided in the main body, so that a processor of the external device may estimate blood pressure, and may output the estimated blood pressure value through an output device of the external device and/or a sound output module provided in in the main body of the ear-wearable device 1000.

The present disclosure can be realized as a computer-readable code written on a computer-readable recording medium. The computer-readable recording medium may be any type of recording device in which data is stored in a computer-readable manner.

Examples of the computer-readable recording medium include a ROM, a RAM, a CD-ROM, a magnetic tape, a floppy disc, an optical data storage, and a carrier wave (e.g., data transmission through the Internet). The computer-readable recording medium can be distributed over a plurality of computer systems connected to a network so that a computer-readable code is written thereto and executed therefrom in a decentralized manner. Functional programs, codes, and code segments needed for realizing the present invention can be readily deduced by programmers of ordinary skill in the art to which the invention pertains.

The present disclosure has been described herein with regard to preferred embodiments. However, it will be obvious to those skilled in the art that various changes and modifications can be made without changing technical conception and essential features of the present disclosure. Thus, it is clear that the above-described embodiments are illustrative in all aspects and are not intended to limit the present disclosure.

What is claimed is:

1. An apparatus for estimating blood pressure comprising:
a photoplethysmogram (PPG) sensor configured to measure a PPG signal from an object;
a force sensor configured to measure a force signal acting between the object and the PPG sensor;
a processor configured to:
divide a predetermined blood pressure range into a plurality of classes,
input the measured PPG signal and the measured force signal into a blood pressure estimation model to obtain probability values for each of the classes, and
estimate blood pressure based on the obtained probability values for the respective classes; and
an output interface configured to provide a user with information on the estimated blood pressure through at least one of a display, an audio output device, and a haptic device,
wherein the processor obtains a blood pressure value by calculating an inner product between a vector of the probability values for the respective classes and a vector of representative values for the respective classes,
wherein the processor is configured to (i) collect a plurality of training data including training signals, including a training PPG signal and a training force signal, and a target blood pressure, constructs a training dataset for the respective classes by labeling the target blood pressure of the collected training data according to the respective classes, and (ii) train the blood pressure estimation model based on deep learning by using the constructed training dataset, and
wherein the processor is configured to train the blood pressure estimation model by using an additive margin softmax loss function.

2. The apparatus of claim 1, wherein the blood pressure estimation model is based on at least one of Deep Neural Network (DNN), Convolution Neural Network (CNN), and Recurrent Neural Network (RNN).

3. The apparatus of claim 1, wherein the processor is configured to set, as the representative value for the respective classes, at least one of a median value, a mean value, a maximum value, and a minimum value in a blood pressure range of the respective classes.

4. The apparatus of claim 1, wherein the blood pressure estimation model comprises a first convolution layer to which the PPG signal is input, a second convolution layer to which the force signal is input, a first pooling layer connected to the first convolution layer, a second pooling layer connected to the second convolution layer, a connected layer connecting an output of the first pooling layer and an output of the second pooling layer to output a feature, and a dense layer outputting probability values for the respective classes by using the feature as an input.

5. The apparatus of claim 1, wherein the processor is configured to perform one-hot encoding on the respective classes of the labeled target blood pressure, and constructs the training dataset including a result of the one-hot encoding and the training signals.

6. The apparatus of claim 1, wherein by using a cross-entropy loss function, the processor is configured to train the blood pressure estimation model.

7. A method of estimating blood pressure, the method comprising:
measuring a photoplethysmogram (PPG) signal for estimating blood pressure from an object;
measuring a force signal acting between the object and a PPG sensor during measurement of the PPG signal for estimating blood pressure;
dividing a predetermined blood pressure range into a plurality of classes;
inputting the measured PPG signal and the measured force signal into a blood pressure estimation model to obtain probability values for each of the classes;
estimating blood pressure based on the obtained probability values for the respective classes,
providing a user with information on the estimated blood pressure through at least one of a display, an audio output device, and a haptic device;
collecting a plurality of training data including training signals, including a training PPG signal and a training force signal, and a target blood pressure;
constructing a training dataset for the respective classes by labeling the target blood pressure of the collected training data according to the respective classes; and
training the blood pressure estimation model based on deep learning by using the constructed training dataset,
wherein the estimating of the blood pressure comprises obtaining a blood pressure value by calculating an inner product between a vector of the probability values for the respective classes and a vector of representative values for the respective classes,
wherein the training the blood pressure estimation model comprises using an additive margin softmax loss function.

8. The method of claim 7, wherein the blood pressure estimation model is based on at least one of Deep Neural Network (DNN), Convolution Neural Network (CNN), and Recurrent Neural Network (RNN).

9. The method of claim 7, wherein the representative value for the respective classes is set as at least one of a median value, a mean value, a maximum value, and a minimum value in a blood pressure range of the respective classes.

10. The method of claim 7, wherein the blood pressure estimation model comprises a first convolution layer to which the PPG signal is input, a second convolution layer to which the force signal is input, a first pooling layer connected to the first convolution layer, a second pooling layer connected to the second convolution layer, a connected layer connecting an output of the first pooling layer and an output of the second pooling layer to output a feature, and a dense layer outputting probability values for the respective classes by using the feature as an input.

11. The method of claim 7, wherein the constructing of the training dataset comprises performing one-hot encoding on the respective classes of the labeled target blood pressure, and constructing a training dataset including a result of the one-hot encoding and the training signals.

12. The method of claim 7, wherein the training of the blood pressure estimation model comprises, by using a cross-entropy loss function, training the blood pressure estimation model.

13. The method of claim 7, wherein the training of the blood pressure estimation model comprises, by using the additive margin softmax loss function, training the blood pressure estimation model.

* * * * *